(12) United States Patent
Van Niekerk

(10) Patent No.: US 7,736,419 B2
(45) Date of Patent: Jun. 15, 2010

(54) PURIFICATION OF POLLUTED AIR

(75) Inventor: Erasmus Van Niekerk, Courcerault (FR)

(73) Assignee: BBR Biofiltrations (Proprietary) Limited, Kempton Park (ZA)

( * ) Notice: Subject to any disclaimer, the term of this patent is extended or adjusted under 35 U.S.C. 154(b) by 480 days.

(21) Appl. No.: 10/594,138

(22) PCT Filed: Mar. 24, 2005

(86) PCT No.: PCT/IB2005/051202

§ 371 (c)(1),
(2), (4) Date: Jun. 4, 2007

(87) PCT Pub. No.: WO2005/092398

PCT Pub. Date: Oct. 6, 2005

(65) Prior Publication Data

US 2008/0017028 A1    Jan. 24, 2008

(30) Foreign Application Priority Data

Mar. 24, 2004    (ZA)    ................................. 2004/2316

(51) Int. Cl.
*B01D 47/02*    (2006.01)

(52) U.S. Cl. ................................. 95/36; 95/108; 96/235
(58) Field of Classification Search .................... 95/36, 95/108; 96/235
See application file for complete search history.

(56) References Cited

U.S. PATENT DOCUMENTS

| 4,472,181 A | 9/1984 | Herrlander |
| 5,618,430 A * | 4/1997 | Fuchs ......................... 210/616 |
| 6,403,366 B1 | 6/2002 | Kim |

FOREIGN PATENT DOCUMENTS

| DE | 2237929 | 2/1974 |
| DE | 147721 | 7/1985 |
| SU | 1287923 | 2/1987 |

* cited by examiner

*Primary Examiner*—Robert J Hill, Jr.
*Assistant Examiner*—Christopher P Jones
(74) *Attorney, Agent, or Firm*—RatnerPrestia

(57) ABSTRACT

A process for purifying polluted air includes passing the polluted air through a fluidized bed of micro-organism-containing particulate media. As the polluted air passes through the fluidized bed, organic pollutants therein are decomposed by the micro-organisms. Purified air containing a lower level of the organic pollutants than the polluted air that enters the fluidized bed, emerges from the fluidized bed.

5 Claims, 2 Drawing Sheets

PURIFICATION OF POLLUTED AIR

CROSS REFERENCE TO RELATED APPLICATIONS

This application is the U.S. national phase filing of International Application No. PCT/IB2005/051202, filed Mar. 24, 2005, and claims priority of Application No. ZA 2004/2316, filed Mar. 24, 2004.

SUMMARY OF THE INVENTION

THIS INVENTION relates to the purification of polluted air. It relates in particular to a process for purifying polluted air, and to air purification apparatus.

According to a first aspect of the invention, there is provided a process for purifying polluted air, which process includes passing polluted air through a fluidized bed of micro-organism-containing particulate media so that, as the polluted air passes through the fluidized bed, organic pollutants therein are decomposed by the micro-organisms, with purified air containing a lower level of the organic pollutants than the polluted air that enters the fluidized bed, emerging from the fluidized bed.

The micro-organism-containing particulate media may comprise inert particles coated with an active medium or biomass. The inert particles may be of inert plastics material such as polypropylene. While the particles may be of substantially uniform size, shape and specific gravity throughout the fluidized bed, a range of particle sizes, shapes and specific gravities, may instead be provided. Thus, for example, the particles may range from sub-micron dust to particles of about 5 mm, ie particles that can pass through 5 mm mesh openings.

The active medium or biomass thus typically decomposes the organic pollutants into carbon dioxide and water. In other words, biofiltration of the polluted air takes place in the fluidized bed.

Preferably, the air that passes through the bed of particulate media acts also as fluidizing medium for the particulate media. The velocity of the air will thus be sufficient to keep the particulate means in a fluidized state. Thus, the air velocity or air flow rate may be from about 0.7 m/s to about 1.5 m/s, typically about 1.0 m/s. The Applicant has found that, for particulate media as hereinbefore described, a minimum air flow rate of about 0.7 m/s is required in order to obtain fluidization, while there is insufficient contact time between the media and the air if the air flow rate exceeds about 1.5 m/s.

The process may include maintaining an aerobic condition or environment within the fluidized bed; however, the fluidized bed is preferably maintained at or near an anaerobic condition or environment. This may be achieved by controlling the humidity in the fluidized bed at an appropriate level.

The process may include simultaneously agitating the fluidized bed to ensure a homogeneous distribution of the active biomass throughout the bed. The agitation may be effected by means of mechanical stirring of the fluidized bed.

The process may also include conditioning the polluted air before passing it into and through the fluidized bed. In particular, the conditioning may comprise moistening the polluted air, to ensure that the air has a sufficiently high moisture content for efficient biofiltration in the fluidized bed, to assist in maintaining the near anaerobic condition in the fluidized bed, and to ensure that the particulate media are kept moist at all times. The moistening will also ensure that the polluted air is at a desired temperature, eg within a temperature range of 20° C. to 40° C., ie it serves to cool down the polluted air.

If desired, a surfactant can be added to the water used for the moistening, to solubilize water insoluble pollutants in the air.

According to a second aspect of the invention, there is provided air purification apparatus, which includes a vessel providing an air purification chamber, with the vessel being adapted such that polluted air can enter the air purification chamber at a low level while purified air can exit the air purification chamber at a higher level; and a plurality of micro-organism-containing particulate media in the air purification chamber, the particulate media being capable of being fluidized by air which passes through the air purification chamber.

The vessel may comprise an operatively upright cylindrical wall component; an apertured or perforated floor spanning the inside of the wall component, with the openings in the floor constituting air inlet openings; and an apertured or perforated roof also spanning the inside of the wall component and spaced from the floor, with the openings in the roof constituting air outlet openings, and with the air purification chamber thus defined between the wall, the floor and the roof.

The apparatus may include agitation means in the air purification chamber, for agitating a fluidized bed of the particulate media which forms in the air purification chamber, in use. The agitation means may comprise a mixer. The mixer may comprise an axially located drive shaft; drive means, such as an electric motor and gearbox combination, for driving the shaft to rotate; and at least one paddle or the like attached to the shaft within the air purification chamber, so that the paddle rotates about the rotational axis of the shaft as the shaft rotates. A plurality of the paddles may be provided, with the paddles being spaced apart in the axial direction and/or around the shaft.

The apparatus may also include an air conditioning chamber below the air purification chamber, when the vessel is located uprightly. The floor of the air purification chamber may constitute the roof of the conditioning chamber, or a separate conditioning chamber roof, spaced from the air purification chamber floor, may be provided, in which case the conditioning chamber roof will also be apertured or perforated to permit air passage therethrough. A perforated or apertured conditioning chamber floor, spaced from its roof, may also be provided, with a cylindrical vessel wall component being provided between the conditioning chamber roof and floor. Air/liquid contact means, such as scrubber packing material, may be provided in the conditioning chamber. Water distribution means for introducing water into or onto the air/liquid contacting means, may also be provided in the conditioning chamber. In use, the moistened air/liquid contacting means will serve to moisten polluted air passing through it.

An air inlet chamber may be provided below the conditioning chamber, with the floor of the conditioning chamber constituting the roof of the air inlet chamber. An imperforate base, spaced from the air inlet chamber roof, and a cylindrical vessel wall component extending between the base and air inlet chamber roof, may be provided. An air inlet may be provided in the vessel wall component. In use, a reservoir of water will be provided above the base and below the air inlet. Water level control means, a water filter and a water pump, for pumping water from the reservoir to the water distribution means in the conditioning chamber, may be provided in the air inlet chamber. It will be appreciated that the apertured roof of the air inlet chamber will permit excess water to pass from the conditioning chamber back into the reservoir.

A purified air chamber may be provided above the air purification chamber, with the roof of the air purification chamber constituting a floor of the purified air chamber. An imperforate roof, spaced from the purified air chamber floor, and a cylindrical vessel wall component between the purified air chamber floor and its roof, may be provided. A purified air outlet may be provided in the purified air chamber roof.

The drive means of the mixer may be located in the purified air chamber, with the drive shaft extending from the purified air chamber roof to the air inlet chamber base and being rotatably mounted thereto. The agitation means may also include a brush paddle attached to the drive shaft and arranged to brush particulate media which is entrained with purified air and separated from the air by the air purification chamber roof, from said roof.

The invention will now be described by way of example, with reference to the accompanying drawings.

DETAILED DESCRIPTION OF THE INVENTION

Figure 1:
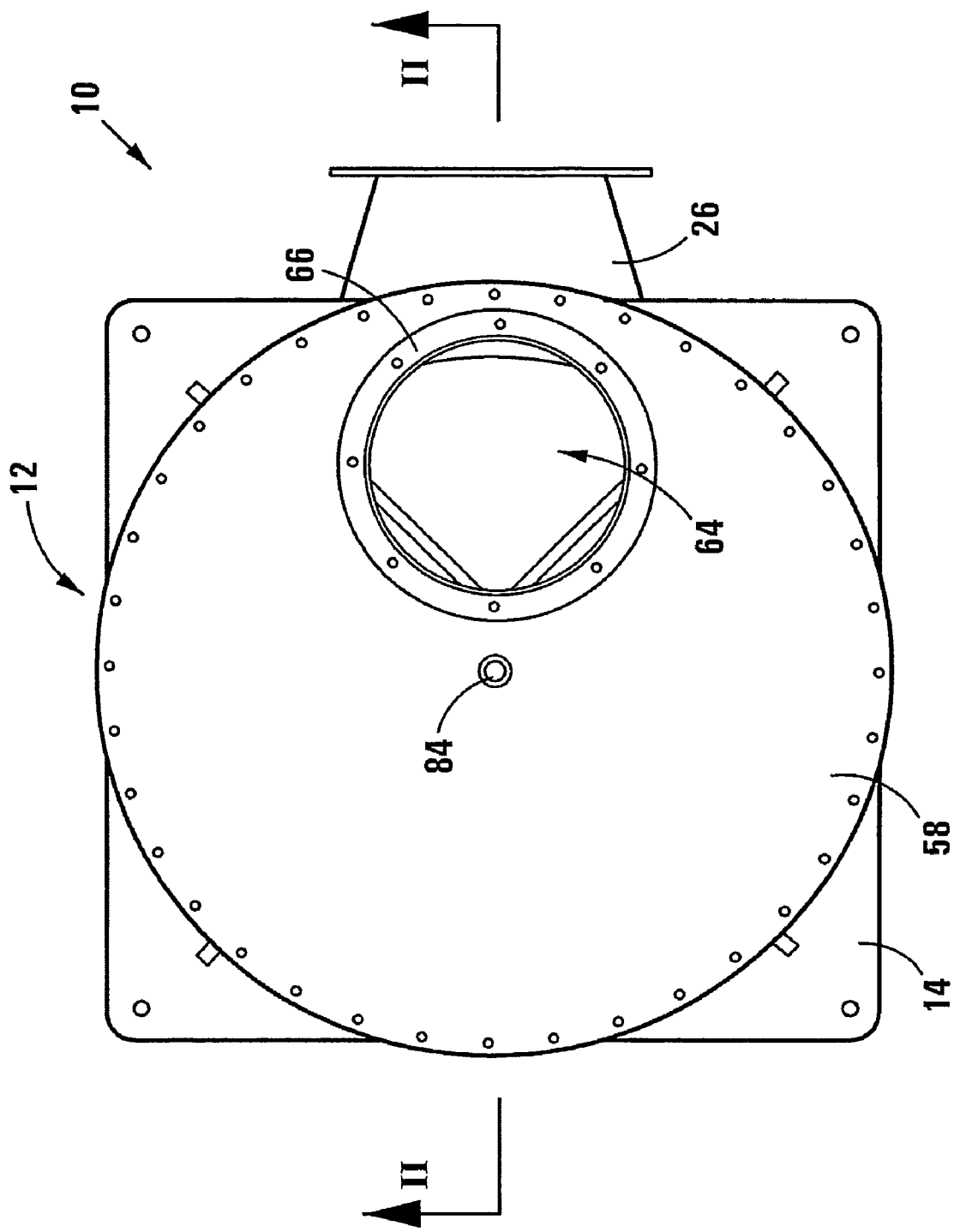
FIG. 1 shows a plan view of an air purification apparatus according to the invention.
Figure 2:
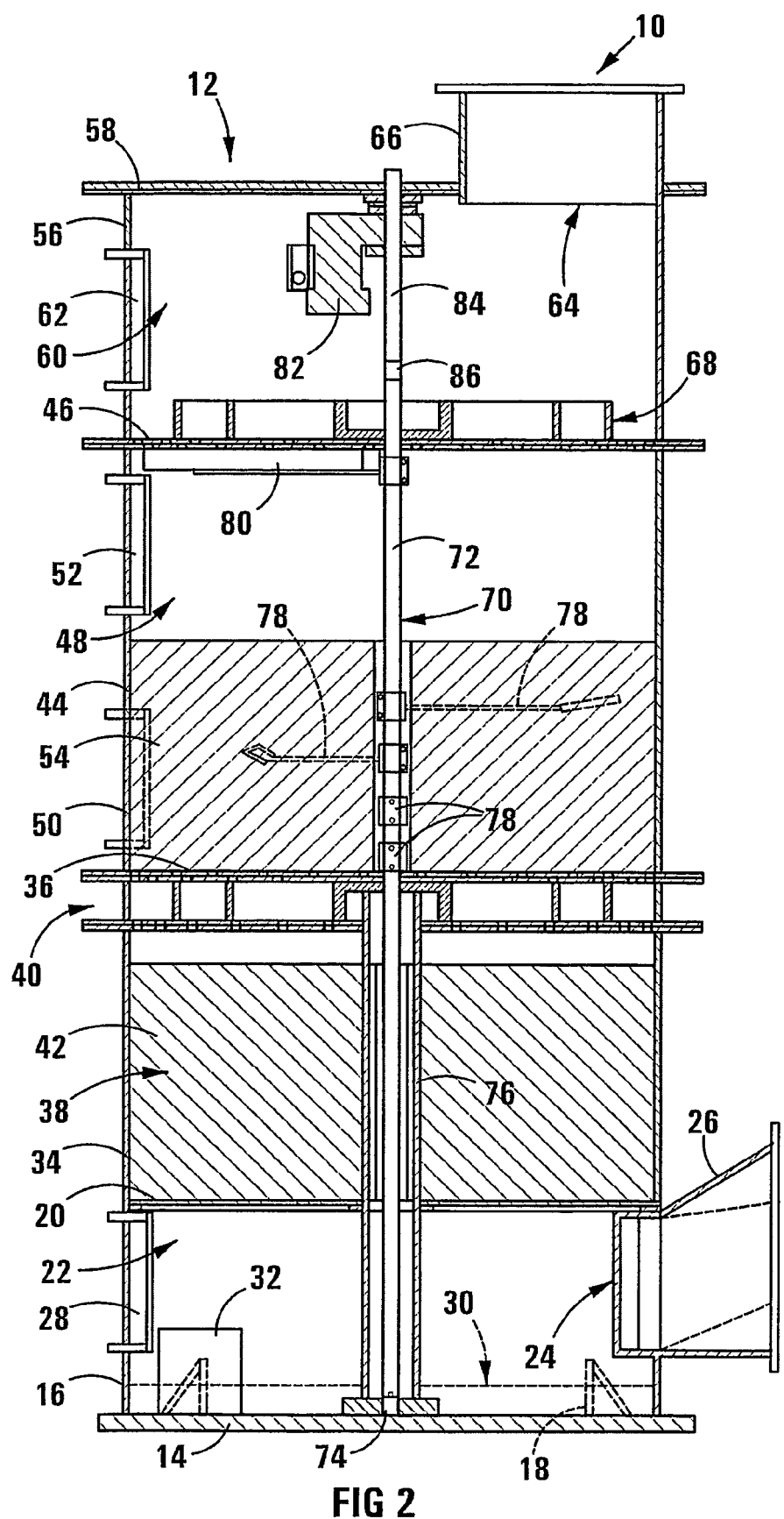
FIG. 2 shows an axial sectional view through II-II in FIG. 1.

In the drawings, reference numeral 10 generally indicates an air purification apparatus according to the invention.

The apparatus 10 includes an upright cylindrical vessel, generally indicated by reference numeral 12. The vessel 12 includes a flat base or base plate 14 to which is mounted a first circular cylindrical wall component 16. The wall component 16 is supported by spaced struts 18. The upper end of the wall component 16 is closed off with an apertured or perforated plate 20. An air inlet chamber 22 is thus defined between the base 14, the plate 20 and the wall section 16, with the plate 20 constituting a roof of the air inlet chamber 22. An air inlet opening 24 is provided in the wall section 16 adjacent the roof 20, with a connection 26 provided around the air inlet opening 24, to permit connection of a foul or polluted air conduit (not shown) to the apparatus 10. An access door 28 is also provided in the wall section 16, adjacent the roof 20.

A reservoir 30 of water will, in use, be contained in the chamber 22 immediately above the base 14. The chamber 22 also includes a housing 32 containing a water level controller (not shown), a circulation pump (not shown) and a water cartridge filter (not shown).

A cylindrical wall component 34 is mounted on the plate 20, with a perforated plate 36 closing off the upper end of the wall component 34. An air conditioning chamber, generally indicated by reference numeral 38, is defined between the plate 20 which thus constitutes the floor of the chamber 38, the wall component 34 and the plate 36, which thus constitutes a roof of the chamber 38. The roof 36 is supported by a support structure, generally indicated by reference numeral 40. The chamber 38 includes, scrubber packing material 42, with a water distribution manifold (not shown) located above the packing 42. Low pressure high volume nozzles (not shown) are mounted to the manifold and arranged so as to spray water onto the packing material 42. The water distribution manifold is connected to the water pump in the chamber 22.

A cylindrical wall component 44 is mounted to the plate 36, so that the plate 36 constitutes a floor therefor. A further perforated plate 46 closes off the upper end of the wall component 44. An air purification chamber, generally indicated by reference numeral 48, is thus defined between the floor 36, the wall 44 and the plate 46, which thus constitutes a roof of the air purification chamber 48. The wall section 44 is provided with a pair of access doors 50, 52.

A bed 54 of micro-organism-containing particulate media is provided inside the chamber 48.

A further water distribution manifold (not shown) is provided in the air purification chamber 48 for spraying water onto the particulate media. This manifold is also connected to the water pump in the air inlet chamber 22.

A cylindrical wall component 56 is mounted to the plate 46, which thus constitutes a floor therefor. An imperforate roof 58 closes off the upper end of the wall component 56. A purified or clean air chamber 60 is defined between the floor 46, the wall component 56 and the imperforate plate 58, which thus constitutes a roof of the chamber 60. An access door 62 is provided in the wall component 60. An air outlet opening 64 is provided in the roof 58, with a flanged connector 66 protruding from the roof 58 around the opening 64. A support structure, generally indicated by reference numeral 68 is provided on top of the floor 46.

The apparatus 10 also includes a mixer, generally indicated by reference numeral 70. The mixer 70 includes an axially located drive shaft 72 extending almost the full length of the vessel 12, with the lower end of the drive shaft 72 rotatably mounted to the base 14 by means of a thrust bearing 74. A tubular housing or sleeve 76 is provided around the lower end portion of the drive shaft 72, with the upper end of the sleeve 76 terminating in the support structure 40. Within the air purification chamber 48 a plurality of mixing paddles 78 are mounted to the drive shaft 72. The paddles 78 are spaced angularly apart as well as longitudinally apart along the drive shaft 72. Immediately below the roof 46 of the air purification chamber 48, a brush paddle 80 is mounted to the drive shaft 72.

The mixer 70 also includes an electric motor/reduction gearbox combination 82 located in the clean air chamber 60, for driving the shaft 72 to rotate. The combination 82 has an axially located drive shaft 84 mounted to the roof 58 by means of a bearing arrangement, and coupled to the main drive shaft 72 by means of a coupler 86.

The wall components 16, 34, 44 and 56 are typically of high density polypropylene, with all mechanical parts, such as the perforated plates 20, 36 and 46, being of stainless steel.

The apparatus 10 also includes an automatic process controller (not shown) for controlling its operation. The process controller is connected to appropriate instruments such as pressure sensors (not shown) in the clean air chamber 60 and in the connector 66, a temperature probe in the conditioning chamber 38 above the packing material 42, and magnetic circuit breakers on the access doors and the drive shaft 72.

On assembling the apparatus 10, the micro-organism-containing particulate media are prepared by placing polypropylene particles or beads, ranging in size from sub-micron dust to 5 mm beads, ie beads capable of passing through 5 mm mesh openings, in a container and thoroughly mixing them with a suitable active medium or biomass, such as composted cattle manure, in a mass proportion of 4 parts by mass plastic beads to 1 part by mass biomass. The mixture is carefully sprayed with water, with sufficient water being used to moisten the biomass without drenching or soaking it. While the water spraying takes place, the mixing is continued. Thereafter, porcelain powder, as an inorganic binder, is added to the mixture with continuous mixing and continuous water addition to ensure that the resultant particulate mixture, comprising micro-organism-containing particulate media, is humid but not so wet that it contains free moisture. The media thus comprises the plastics particles or beads coated with a film of the biomass. The air purification chamber 48 is typically filled to a height of about 400 mm with the particulate media.

The polypropylene beads can, for example, be disc-shaped and have dimples in their outer surfaces. The discs typically have a diameter of about 4 mm and a thickness of about 2 mm; however, as mentioned hereinbefore, the bed will typically contain from sub-micron beads up to 5 mm beads.

Instead of using porcelain powder as the inorganic binder, any other suitable inorganic binder can be used, eg bentonite.

It is, however, believed that the shape, size and texture of the plastics beads are not critical, provided that they are fluidizable and coatable with the biomass substrate. In other words, the surface finish of the beads must be sufficiently rough to accept a coating of the biomass. Additionally, the thicknesses of the biomass coatings or films on the plastics particles are believed not to be critical provided that the films or coatings are not too thin so that optimum activity cannot be obtained nor too thick so that anaerobic conditions prevail inside the coatings or films.

If necessary, the biomass coated plastics particles are seeded with active micro-organisms, before start-up of the reactor. Naturally occurring bacteria are present in the atmosphere, and for applications requiring the use of such bacteria or micro-organisms in the biomass of the particulate media, no seeding of the particulate media is required.

However, for organic pollutants or volatile organic compounds such as solvents or other chemicals in the polluted air, bacteria or micro-organisms capable of breaking down these pollutants do not occur naturally in the air, and the particulate media must thus be seeded with appropriate commercially available bacteria.

In use, a contaminated air stream is moved from a source of the contamination, through a fan and ducting system, to the inlet 24 to the chamber 22. The contaminated or foul air moves upwardly through the apertured floor 20 into the conditioning chamber 38. At the same time, water is pumped from the reservoir 30 and sprayed onto the scrubbing media 42 by means of low pressure high volume nozzles. The scrubber packing material or conditioning media typically comprises commercially available plastic cones that ensure even distribution of water sprayed onto the cones and that ensure maximum contact of the upwardly moving air stream with the water. This ensures that a high moisture content is imparted to the air stream before it enters the air purification chamber 54 through the plate 36. The water in the reservoir 30 is dosed with a surfactant, using a metering pump (not shown), to ensure that all organic components in the contaminated air are rendered water soluble, ie are solubilized. Additionally, the water serves to cool down the air stream to a temperature of 20° to 40°.

The thus conditioned air enters the bed 54 of micro-organism-containing particulate media in the purification zone 48, and passes upwardly through the bed at a velocity of about 1 m/s. This is sufficient to ensure that the bed 54 is fluidized. The air thus passes through the fluidized bed with high turbulence, which ensures that the contaminant organic molecules in the air stream make optimal contact with the moist film of bioactive media on the plastics particles. The contaminant molecules dissolve in the water film where the micro-organisms live, thereby making them available for consumption and conversion or decomposition to carbon dioxide and water. Simultaneously, continuous mixing by means of the paddles or blades 78 ensures that the fluidized particulate media are moved outwardly and upwardly. This ensures that the biofilms of the particulate media are constantly in contact with contaminated air as the particulate media move from the bottom to the top of the bed 54.

The fluidized bed 54 functions under aerobic conditions; however, it is controlled so that it is operated at near-anaerobic condition. This is achieved by maintaining a high humidity level within the fluidized bed. The high humidity level is in turn controlled by applying a low voltage current over the particulate media in a simple electric circuit (not shown). A change in moisture content in the bed, which will result in a humidity change, causes a change in voltage over the media bed. This signal is calibrated and sent to the process controller, which then regulates the water injected directly into the fluidized bed through the further water distribution manifold.

Typically, the mixer 70 rotates at a mixing speed of about 4 rpm. However, it is believed that this mixing speed is not critical and the mixing speed can thus vary, eg typically between 2 rpm and 5 rpm.

Clean air exits from the top of the bed and leaves the apparatus 10 through the opening 64. Any entrained particulate media are separated from the clean air by means of the perforated plate 46, and are scraped from the undersurface of the plate by means of the paddle 80.

The combination of the fluidized bed and the mixing achieved with the mixer 70, in the purification chamber 48, ensures that the micro-organism population, treatment temperature and humidity within the bed 54 remain substantially homogeneous throughout the bed. It also prevents channeling and dry spots normally associated with known static or fixed bed biofilters.

In the clean air chamber 60, the air flow rate is measured continuously. An air flow signal is sent to the process controller which will control the air flow to ensure that it stays within the design flow for the apparatus 10.

The pressure drop through the apparatus 10 is in the order of 20 mbar (2000 Pa) during continuous operation with a pressure drop of about 24 mbar at start-up. Thus, polluted air having a relatively low inlet pressure can be treated in the apparatus 10.

The apparatus 10 can handle a pollutant or contaminant load (organic compounds) of up to about 1000 ppm, and typically has a removal efficiency of >95%.

The apparatus 10 is, it is believed, unique in that it uses a fluidized bed 54 of micro-organism-containing particulate media. The fluidized bed 54 is continuously agitated by means of the mixer 70 to ensure 100% homogeneous distribution of the biomass, with an equal population of micro-organisms throughout the bed. As stated hereinbefore, the temperature and moisture content of the particulate media is process controlled at an optimum level to ensure maximum activity and population of the micro-organisms, ie all micro-organisms throughout the bed come into contact with contaminants in the air stream due to the continuous movement of the particulate media from the bottom to the top of the bed.

The process controller can be located remotely from the apparatus 10 and, if desired, a telephone system may be connected to the process controller. The process controller can then transmit performance data and problem reporting to another computer or even automatically call a maintenance person on a numeric pager in case of a problem. This option may be useful for applications where the process is critical, such as when poisonous gases are being processed or where large penalties are imposed by local authorities for off-specification gases.

The apparatus 10 is thus a high performance biofilter or air filtration device designed to remove water soluble organic compounds and odours from polluted or foul air. The apparatus 10 can process upwards of 10000 m$^3$ of contaminated air per m³ of particulate media compared to approximately 125 m³ per m³ of biomass or particulate media in the case of fixed or static bed biofilters. Typically, the apparatus 10 can be sized to handle 1600, 3000 or 6000 m³/hr of polluted air.

An apparatus 10 capable of handling 3000 m³/hr of contaminated air requires a footprint of only 1.2 m×1.2 m, and a height of 2.2 m, and has a mass of less than 500 kg, compared to a fixed bed biofilter of equivalent capacity which requires a steel or concrete structure of about 6 m×4 m and 2 m high, and has a mass of 20 to 30 tonnes. Thus, the apparatus 10 of the present invention can be installed in a confined area such as on a rooftop, in a basement or in a service shaft.

The apparatus 10 is relatively simple to install and to operate. The only external requirements are a 3-phase electrical power source, a water supply, a sewer drain, and air inlet and outlet ducting.

It is believed that the apparatus 10 can handle polluted or contaminated air emanating from restaurants, petroleum refining plants, food production plants, composting plants, waste water treatment plants, or any other processes that produce air polluted with organic pollutants.

It is believed that the process of the invention provides a near-perfect environment for microbial biodegradation of organic contaminants in polluted air, to take place on a constant basis. It was surprisingly found that, in the process of the invention, it is possible to fluidize a micro-organism containing particulate media even where the particles differ substantially in size, shape and specific gravity. Another feature of the invention is that the fluidized bed is maintained at aerobic conditions; however, due to the high moisture content that can be maintained, the fluidized bed can be controlled at near-anaerobic conditions. This can be achieved consistently, resulting in high efficiencies.

It was also surprisingly found that with the process of the present invention, a substantially higher transfer rate of pollutants from the air to the micro-organism-containing biomass films on the plastics beads can be obtained than is the case with fixed or static bed biofilters. The transfer rate can typically be up to about 100 times greater than with known fixed bed biofilters.

In the fluidized bed biofiltration of the present invention, optimum conditions for micro-organisms on substantially the entire surfaces of the inert particles are maintained at all times, which means that the micro-organisms can populate the biofilter to capacity and maintain that population throughout a cycle of operation, whereas with static or fixed bed biofilters only a very small part of the filter is active at best, due to the fact that the physical composition and design of the bed of a static biofilter does not permit flow of gas around every particle, nor is it possible to maintain optimum humidity in the entire static filter bed at all times. Thus, in the light of these drawbacks of static biofilter beds, the concentration of micro-organisms is greatest at the entrance zone of the polluted air where there are the most nutrients and humidity, with control of humidification being the single biggest problem in static biofilters. Additionally, compaction, channeling and other slow deterioration problems arise with static filter beds. In contrast, in the process and apparatus of the present invention, these problems are largely avoided. Additionally, in the conditioning chamber, non-water-soluble pollutants are emulsified, and the surface tension of smoke particles in the air reduced so that the particles can rapidly be transferred into the biofilms on the particulate media. As indicated hereinbefore, it was found that when the fluidized bed is 400 mm deep, and the air flow through the bed is 1/s, efficient fluidization is obtained as well as a satisfactory gas to biofilm transfer rate.

The invention claimed is:

1. A process for purifying polluted air, which process includes in a conditioning chamber, conditioning the polluted air by moistening it; allowing the conditioned polluted air to pass from the conditioning chamber into an air purification chamber; and in the air purification chamber, passing the conditioned polluted air through a fluidized bed of micro-organism-containing particulate media while simultaneously stirring the fluidized bed so that, as the conditioned polluted air passes through the fluidized bed, organic pollutants therein are decomposed by the micro-organisms, with purified air containing a lower level of the organic pollutants than the conditioned polluted air that enters the fluidized bed, emerging from the fluidized bed.

2. A process according to claim 1, wherein the micro-organism-containing particulate media comprises inert particles coated with an active medium or biomass.

3. A process according to claim 2, wherein the particles have sizes that range from sub-micron to 5 mm.

4. A process according to claim 1, wherein the air that passes through the bed of particulate media acts also as fluidizing medium for the particulate media, and wherein the air flow rate is from 0.7 m/s to 1.5 m/s.

5. A process according to claim 1, which includes maintaining the fluidized bed at or near anaerobic conditions by controlling the humidity in the fluidized bed.

* * * * *